United States Patent
Paul et al.

(10) Patent No.: US 10,327,821 B2
(45) Date of Patent: Jun. 25, 2019

(54) DEVICES AND METHODS FOR TREATING VERTEBRAL FRACTURES

(71) Applicant: GLOBUS MEDICAL, INC., Audubon, PA (US)

(72) Inventors: David C. Paul, Phoenixville, PA (US); Sean Suh, Morganville, NJ (US)

(73) Assignee: Globus Medical, Inc., Audubon, PA (US)

( * ) Notice: Subject to any disclaimer, the term of this patent is extended or adjusted under 35 U.S.C. 154(b) by 0 days.

(21) Appl. No.: 15/207,528

(22) Filed: Jul. 12, 2016

(65) Prior Publication Data

US 2016/0317197 A1 Nov. 3, 2016

Related U.S. Application Data

(63) Continuation of application No. 14/489,940, filed on Sep. 18, 2014, now Pat. No. 9,414,867, which is a continuation of application No. 12/686,052, filed on Jan. 12, 2010, now Pat. No. 8,864,773.

(60) Provisional application No. 61/144,578, filed on Jan. 14, 2009.

(51) Int. Cl.
*A61B 17/70* (2006.01)
*A61B 17/88* (2006.01)
*A61B 17/34* (2006.01)
*A61B 17/86* (2006.01)

(52) U.S. Cl.
CPC ...... *A61B 17/7095* (2013.01); *A61B 17/3468* (2013.01); *A61B 17/7071* (2013.01); *A61B 17/7074* (2013.01); *A61B 17/7094* (2013.01); *A61B 17/863* (2013.01); *A61B 17/88* (2013.01)

(58) Field of Classification Search
CPC ............ A61B 17/7095; A61B 17/7074; A61B 17/863; A61B 17/88; A61B 17/3468
See application file for complete search history.

(56) References Cited

U.S. PATENT DOCUMENTS

| | | | |
|---|---|---|---|
| 6,319,254 B1 | 11/2001 | Giet et al. | |
| 6,425,887 B1 * | 7/2002 | McGuckin | A61B 17/3417 604/272 |
| 6,629,977 B1 | 10/2003 | Wolf | |
| 2002/0183761 A1 | 12/2002 | Johnson et al. | |
| 2004/0210227 A1 | 10/2004 | Trail et al. | |
| 2005/0187548 A1 | 8/2005 | Butler et al. | |
| 2006/0184246 A1 * | 8/2006 | Zwirkoski | A61B 17/7094 623/11.11 |
| 2007/0083205 A1 * | 4/2007 | Attawia | A61B 17/3472 623/16.11 |
| 2007/0093846 A1 * | 4/2007 | Frigg | A61B 17/025 606/90 |

(Continued)

*Primary Examiner* — Christopher J Beccia

(57) ABSTRACT

The present application is directed to devices and methods for treating vertebral fractures with one or more bone pins. In one embodiment of a method, a fractured vertebral body may be accessed through a pedicle portion and an opening may be created therethrough. One or more bone pins may be inserted through the opening. In one embodiment, at least one of the inserted bone pins is inserted to extend across a fracture zone with a proximal portion of the pin engaging a first bone segment and a distal portion engaging a second bone segment. The pin or pins may be manipulated to immobilize the first and second portions of the fractured vertebra.

19 Claims, 10 Drawing Sheets

(56) References Cited

U.S. PATENT DOCUMENTS

| | | | |
|---|---|---|---|
| 2007/0156241 A1* | 7/2007 | Reiley | A61B 17/1615 623/17.11 |
| 2007/0162044 A1* | 7/2007 | Marino | A61B 17/1637 606/96 |
| 2011/0118790 A1* | 5/2011 | Reiley | A61B 17/1615 606/279 |

* cited by examiner

DEVICES AND METHODS FOR TREATING VERTEBRAL FRACTURES

CROSS REFERENCE TO RELATED APPLICATIONS

This Patent Application is a continuation of U.S. patent application Ser. No. 14/478,940, which is a continuation of U.S. patent application Ser. No. 12/686,052, filed Jan. 12, 2010, now issued as U.S. Pat. No. 8,864,773, which claims priority to U.S. Provisional Application No. 61/144,578, filed Jan. 14, 2009, the entire contents of which are herein incorporated by reference in their entireties.

FIELD OF THE INVENTION

A minimally invasive distraction and support device and method would have significant application in orthopaedic surgical procedures, including acute and elective procedures to treat bone fractures and degenerative changes of the skeletal system and including vertebral compression fractures, interbody fusion, vertebral disc augmentation or replacement, and other compression fractures and/or non-orthopaedic surgical procedures.

A vertebral compression fracture is a crushing injury to one or more vertebrae. Vertebral fractures are generally associated with osteoporosis (the "brittle bone" disease), metastasis, and/or trauma. Osteoporosis reduces bone density, thereby weakening bones and predisposing them to fracture.

The osteoporosis-weakened bones can collapse during normal activity. In severe cases of osteoporosis, actions as simple as bending forward can be enough to cause a vertebral compression fracture. Vertebral compression fractures are generally known to be the most common type of osteoporotic fractures. The mechanism of these fractures is one of flexion with axial compression where even minor events may cause damage to the weak bone. While the fractures may heal without intervention, the crushed bone may fail to heal adequately. Moreover, if the bones are allowed to heal on their own, the spine be deformed to the extent the vertebrae were compressed by the fracture. Spinal deformity may lead to breathing and gastrointestinal complications, and adverse loading of adjacent vertebrae.

Vertebral fractures happen most frequently at the thoracolumbar junction, with a relatively normal distribution of fractures around this point. Vertebral fractures can permanently alter the shape and strength of the spine. Commonly, they cause loss of height and a. humped back. This disorder (called kyphosis or "dowager's hump") is an exaggeration of the spinal curve that causes the shoulders to slump forward and the top of the back to look enlarged and humped.

severe cases, the body's center of mass is moved further away from the spine resulting in increased bending moment on the spine and increased loading of individual vertebrae.

Another contributing factor to vertebral fractures is metastatic disease. When cancer cells spread to the spine, the cancer may cause destruction of part of the vertebra, weakening and predisposing the bone to fracture.

Osteoporosis and metastatic disease are common root causes leading to vertebral fractures, but trauma to healthy vertebrae also causes minor to severe fractures. Such trauma may result from a fall, a forceful jump, a car accident, or any event that stresses the spine past its breaking point. The resulting fractures typically are compression fractures or burst fractures.

Vertebral fractures can occur without pain. However, they often cause a severe "band-like" pain that radiates from the spine around both sides of the body. It is commonly believed that the source of acute pain in compression fractures is the result of instability at the fracture site, allowing motion that irritates nerves in and around the vertebrae.

Various instruments and methods for the treatment of compression-type bone fractures and other osteoporotic and/or non-osteoporotic conditions have been developed. Such methods generally include a series of steps performed by a surgeon to correct and stabilize the compression fracture. A cavity is typically formed in the bone to be treated, followed by the insertion of one or more inflatable balloon-likes device into the bone cavity. Inflation of the balloon-like device causes a compaction of the cancellous bone and/or bone marrow against the inner cortical wall of the bone, thereby resulting in enlargement of the bone cavity and/or reduction of the compression fracture. The balloon-like device is then deflated and removed from the bone cavity. A biocompatible filling material, such as methylmethacrylate cement or a synthetic bone substitute, is sometimes delivered into the bone cavity and allowed to set to a hardened condition to provide internal structural support to the bone. In theory, inflation of the balloons restores vertebral height. However, it is difficult to consistently attain meaningful height restoration. It appears the inconsistent results are due, in part, to the manner in which the balloon expands in a compressible media and the structural orientation of the trabecular bone within the vertebra.

For example, it has been found that expansion of the balloon-like device can be difficult to control. Instead, when such a balloon-like device is inflated, expansion occurs along a path of least resistance. As a result, the direction of compaction of the cancellous bone and/or reduction of the compression fracture is not controllable, and expansion occurs in multiple directions and along multiple axes.

SUMMARY OF THE INVENTION

The present application is generally directed to devices and methods for treating vertebral fractures with one or more bone pins. In one embodiment of a method, a fractured vertebral body may be accessed through a pedicle portion and an opening created therethrough. One or more bone pins may be inserted through the opening. At least one of the inserted bone pins may be inserted to extend across a fracture zone with a proximal portion of the pin engaging a first bone segment and a distal portion engaging a second bone segment. The pin or pins may be manipulated to immobilize the first and second portions of the fractured vertebra.

In another embodiment, a system for treating a fractured vertebral bone is disclosed. This system generally comprises a cannulated eyelet configured and dimensioned for installation in a pedicle portion of the vertebral bone to create an access opening into the interior portion of the vertebral body. An elongate cannula may be releasably mountable to the eyelet. The cannula may be moveable over 60 degrees of angulation with respect to the eyelet when mounted thereto. The system may also include a plurality of bone pins.

DETAILED DESCRIPTION OF THE ILLUSTRATED EMBODIMENTS

Embodiments of the present invention are generally directed to devices and methods for treating bone fractures. In particular, certain embodiments are directed to minimally invasive distraction and support devices and methods to treat fractures of the vertebral body.

Figure 1:
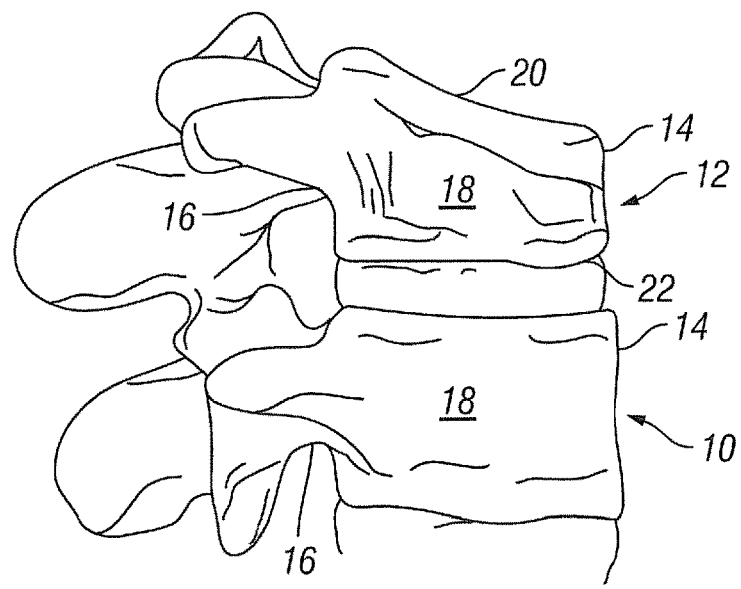
FIG. 1 shows a vertebral body having a compression fracture displacing its superior and anterior edge.
Figure 2:
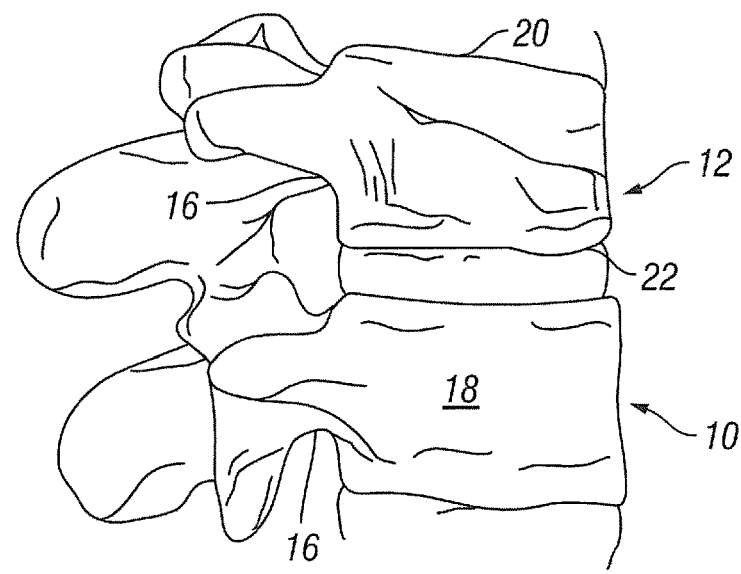
FIG. 2 shows a vertebral body, following treatment of a compression fracture.

The devices and methods are generally described by its application to the vertebral compression fracture, However, in alternate applications, alternate types of fractures including, but not limited to, burst type fractures may also be treated. FIG. 1 illustrates two vertebrae 10, 12, each with an anterior side 14, a posterior side 16, and lateral sides 18 (only one shown). Vertebra 10 is fully intact, while vertebra 12 has a vertebral compression fracture (i.e. the top 20 and bottom 22 of the vertebra have been displaced towards each other). Referring to FIG. 2, the vertebral compression fracture of vertebra 12 is shown in a reduced or height restored state (i.e., the top 20 and bottom 22 of the vertebra 12 are distracted or displaced back to or near their original/intact positions). it is known that the force required to reduce the vertebral compression fracture can often be rather high.

Referring to FIGS. 3-7, one embodiment of a bone fracture distraction device or system 40 is shown. System 40 generally comprises one or more rods, skewers, or pins 42, 62 insertable through a cannula 44 to a vertebral body. In one variation, pin 42 may comprise a partially threaded section 46. In another variation, pins 42 may be completely threaded along its length or completely free from threads. In yet another variation, pins 42 may be cannulated.

Figure 5:
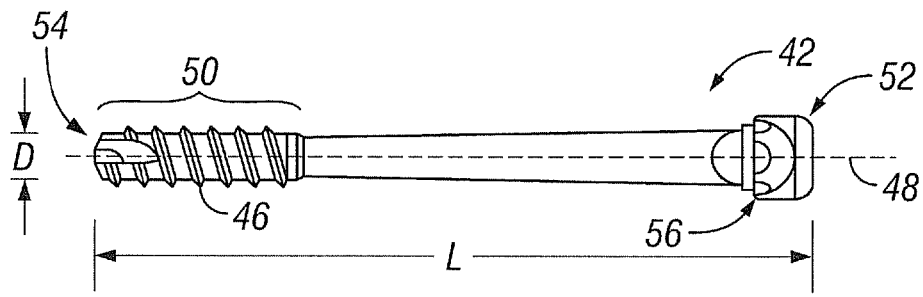
FIG. 5 is a side view of one embodiment of a bone fixation pin according to the invention.
Figure 6:
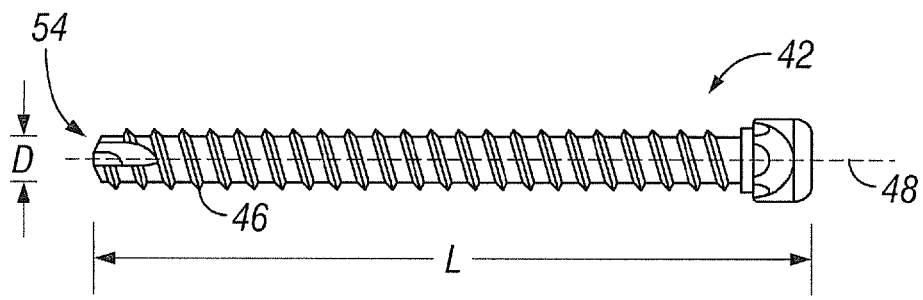
FIGS. 6-7 are side views of alternate embodiments of bone pins according to the invention.
Figure 7:
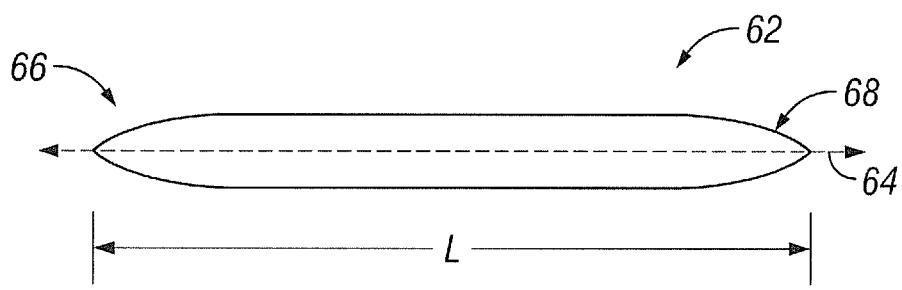

Referring to FIGS. 5-7, exemplary embodiments of pins 42, 62 according to the invention are shown, As shown in FIG. 5, one embodiment of a pin 42 is a generally thin cylindrical member extending along a longitudinal axis 48 and may have a distal end portion 50 with threads 46 and an enlarged head portion 52 adjacent its proximal end 54. A hexagonal shaped indentation may be provided adjacent proximal end 54 to accommodate a corresponding shaped driving tool to facilitate rotation of pin 42 during installation. Referring to FIG. 6, according to certain embodiments, pin 42 may have threads 46 along its entire length. In general when installed in a bone, head portion 52 acts in conjunction with threaded portion 46 to draw or compress bone segments together. In one variation, the distal tip 54 may be generally blunt or otherwise configured and dimensioned to engage cortical bone. In one embodiment, head portion 52 may have a flange wall 56 extending generally orthogonal to longitudinal axis 48. In alternative embodiments, flange wall 46 may extend at an angle between about 30 and 45 degrees with respect to longitudinal axis 48, In still other embodiment, pins 42 may not have a head portion at all, such that the pin profile is substantially cylindrical in shape and may have threads along any or all of its length. In this regard, those skilled in the art will appreciate that such a headless pin may facilitate manipulation of bone fragments or bone portions, such as by skewering, piercing and/or pushing or moving the fragment or bone portion.

Referring to FIG. 7, another embodiment of an unthreaded pin 62 is shown. Pin 62 is a generally thin cylindrical member extending along a longitudinal axis 64 and may have a tapered distal and proximal end portions 66, 68. In this regard, pin 62 has a shape similar to a toothpick. The shape and dimensional characteristics of pin 62 facilitate lateral insertion of multiple pins 62 against one another. In operation, such a feature may be utilized to treat bone fractures minimally invasively, as described below.

Pins 42, 62 and cannulated tubes 44 may be provided in kits or sets such that a surgeon user may select among a variety of shaped and sized pins and cannulas to be used in a particular procedure as desired. According to one variation, pins 42, 62 may have a diameter D between about 1 mm and about 4 mm. Pins 42, 62 may have an overall length L between about 10 mm and 65 mm, in one variation, pins 42, 62 may have an overall length L between about 10 mm and 35 mm and may be provided in a kit having, for example, 15 mm, 20 mm, 25 mm, and 30 mm lengths. Cannulas 44 may have diameters between about 4 mm and 8 mm, and may be provided in a kit having, for example, in 5 mm, 6 mm, and 7 mm diameters.

Referring again to FIGS. 3-7, according to one embodiment, cannulated tube 44 may comprise multiple pieces and include a distal end piece 72 having a. threaded exterior portion 74 movably connected to proximal cannula portion 76. In this regard, threaded end piece 72 may be threadedly advanced into the pedicle such that cannula 44 may be semi-permanently docked in position with respect to a vertebral body to be treated. in general, threaded end piece 72 is configured and dimensioned to engage the pedicle in a similar manner to a pedicle screw, except the threaded end piece 72 is generally shorter than a pedicle screw and is cannulated to provide a portal into the interior portion of the vertebral body where the cancellous bone is generally located. Those skilled in the art of spine surgery and pedicle screw installation will be familiar with localizing the threaded end piece 72 into the pedicle. Distal piece 72 may be movably connected to proximal cannula 76 such that cannula 44 may angulate or rotate with respect to distal piece 72 while maintaining communication of the cannulation 45 between the distal piece 72 and proximal cannula 76. According to one variation, any known flexible joint or linkage may be provided between end piece 72 and proximal cannula 76 to facilitate insertion and advancement of pins 42, 62 and/or an installation tool there through.

In operation, cannulated tube 44 may be positioned adjacent a pedicle using known techniques, including minimally invasive methods utilizing a K-wire (not shown). Once the distal piece 72 is docked in the pedicle, a user may move or wand the cannula 44 around as desired depending on the particular application. In this regard, a surgical user may achieve a variety of angles of approach to install one or more pins 42, 62. In one variation, the interior portion of end piece 72 may have an hourglass profile to facilitate smooth transition of a pin through the distal piece 72 when cannula 44 is at an angle. In one variation, cannula 44 may move through a cone angle a of between about 30 to 60 degrees. In another embodiment, one or more openings 79 may be provided along the length of cannula 44 to facilitate angled entry of pins 42, 62 therethrough.

Figure 3:
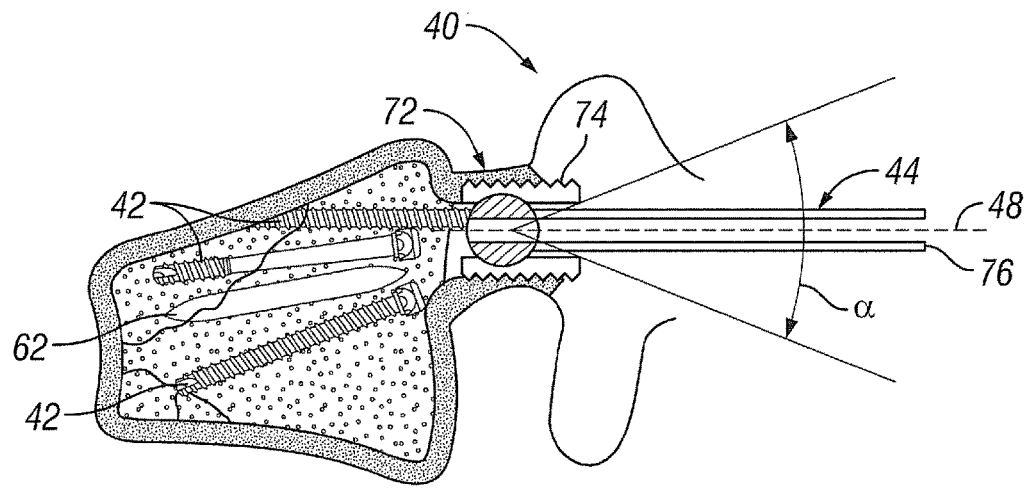
FIG. 3 is a side view of one embodiment of a bone treatment system according to the invention, shown in a vertebral body in a collapsed position.
Figure 4:
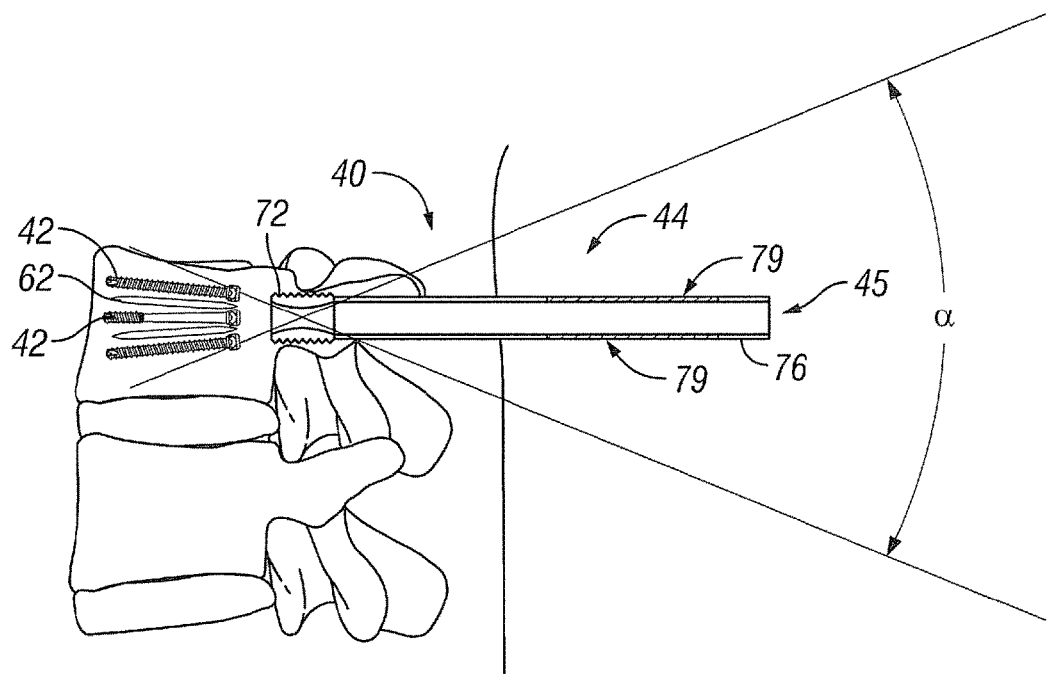
FIG. 4 is a side view of the system of FIG. 3, shown in a vertebral body in a restored position.

Pins 42, 62 described above may be used in any number of surgical methods and applications. Referring to FIGS. 3-4, according to one embodiment of a method according to the invention, one or more pins 42 of system 40 may be positioned at various angles into a collapsed vertebral body (FIG. 3). In one variation, multiple pins 42 may be installed to decompress a vertebral fracture. The cannula 44 of system 40 may be deployed to access the vertebra through the pedicle to provide a working portal into the vertebral body. In one variation, distal end piece 72 of cannula extends through the cortical region of the vertebral body and into the cancellous region. Once such a working portal into the vertebral body is established, one or more pin introduction or pin skewering procedures may take place.

In one method according to the invention, one or more partially threaded pins 42 may be used to join together and/or compress one or more bone segments. For example, with a vertebral body fracture, pin 42 may be threaded through a first bone segment into a second bone segment. In this regard, the bone segments are generally brought into abutting contact to facilitate stitching and/or bone heating. Such a compressive feature may also be used for burst type fractures. In addition, or in the alternative, in another method according to the invention a first bone segment may be separated from another bone segment by displacing or pushing a pin 42 thereagainst. For a vertebral compression fracture, for example, one or more pins 42 may be used to push the compressed portion of the vertebral body in an outward direction and creating a vertical force that displaces the upper or tower end plates of the vertebral body.

Referring again to FIGS. 3-4, one exemplary embodiment vertebral compression fracture treatment is shown using a system 40, One or more pins 42 may be inserted into a vertebral body at one ore more angles. Pins 42 may be threaded and or pushed into the bone portion to be treated through the aforesaid opening provided after installation of cannula 44. Any variety or combination of partially threaded, fully threaded, or unthreaded pins may be installed to compress bone segments or portions and/or manipulate or reposition bone segments. Cannula 44 may be moved to alternative angles and one or more additional pins 42 may be installed within the vertebral cavity as described above until that expansion is complete and the bone treatment device may be fixated in the extended condition. In addition, the cannula 44 may then be disconnected from the distal end piece 72, or in the alternative distal end piece 72 may be unthreaded and removed from the pedicle. Once installed, the pins 42 are generally configured. and dimensioned to stretch the vertebra substantially to its original dimension, as it were.

Figure 8:
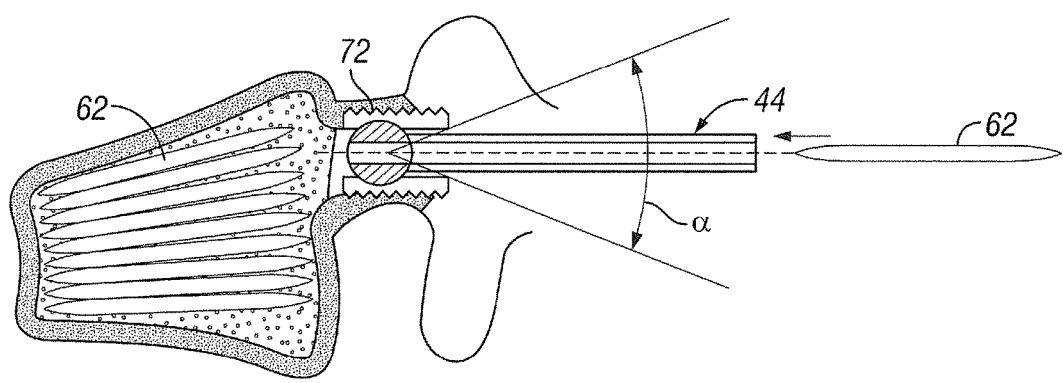
FIGS. 8-9 are side views of another embodiment of a bone treatment system according to the invention.
Figure 9:
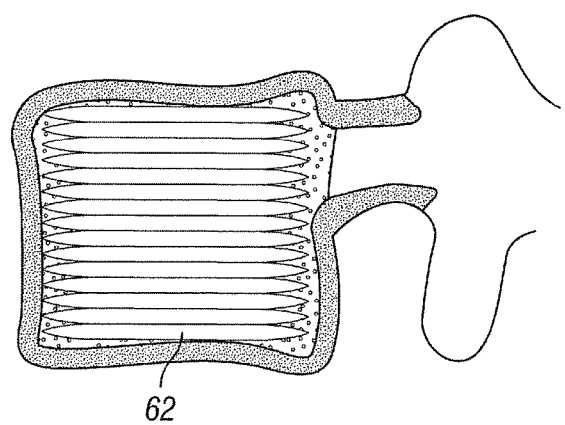

Referring to FIGS. 8-9, another method according to the invention is shown. According to one embodiment, a multitude of pins 62 may be sequentially inserted into a fractured vertebral body, as shown in FIG. 8, this regard, pins 62 function similar to a toothpick being inserted into a toothpick container as they are generally easily inserted in an insertion direction along an axis of cannula 44. At the same time, as the volume of the vertebral body is filled, a vertical decompressive force is gradually transmitted to the end plates to force the end plates apart and decompress the compression fracture, as shown in FIG. 9.

Figure 10:
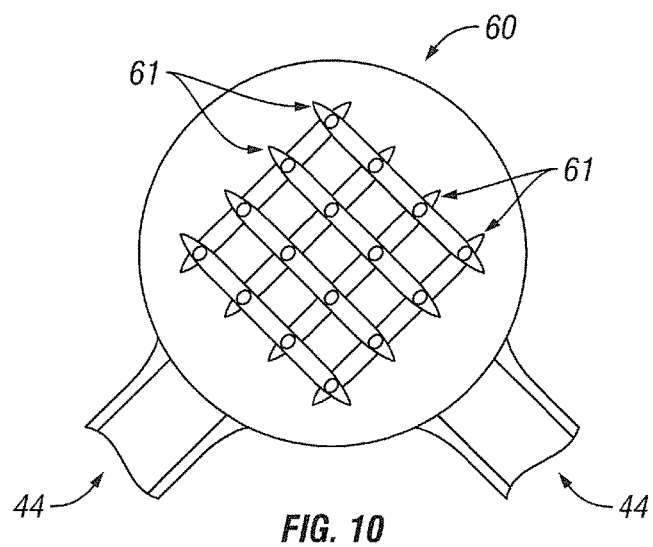
FIGS. 10-13 are views of another embodiment of a bone treatment system according to the invention.
Figure 11:
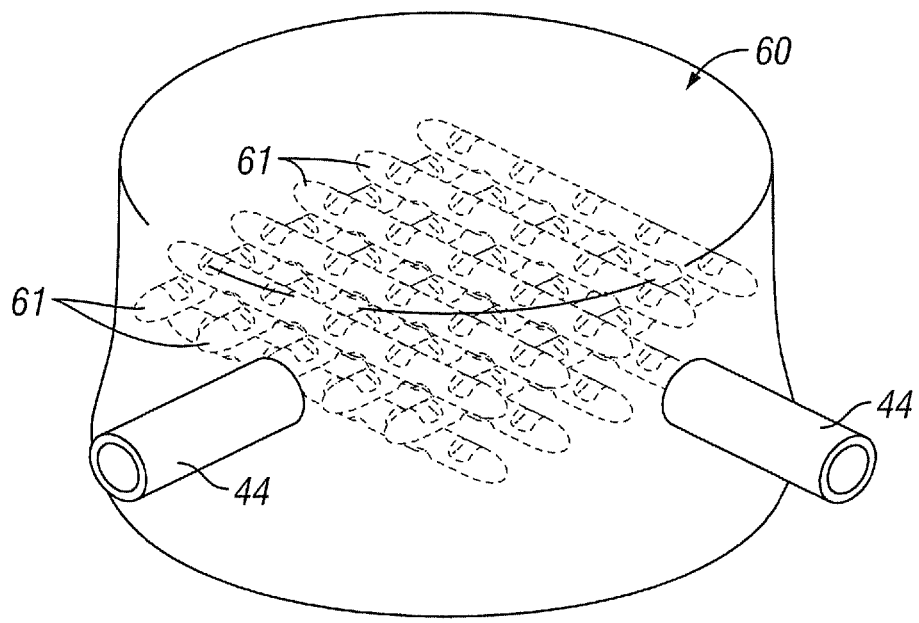
Figure 12:
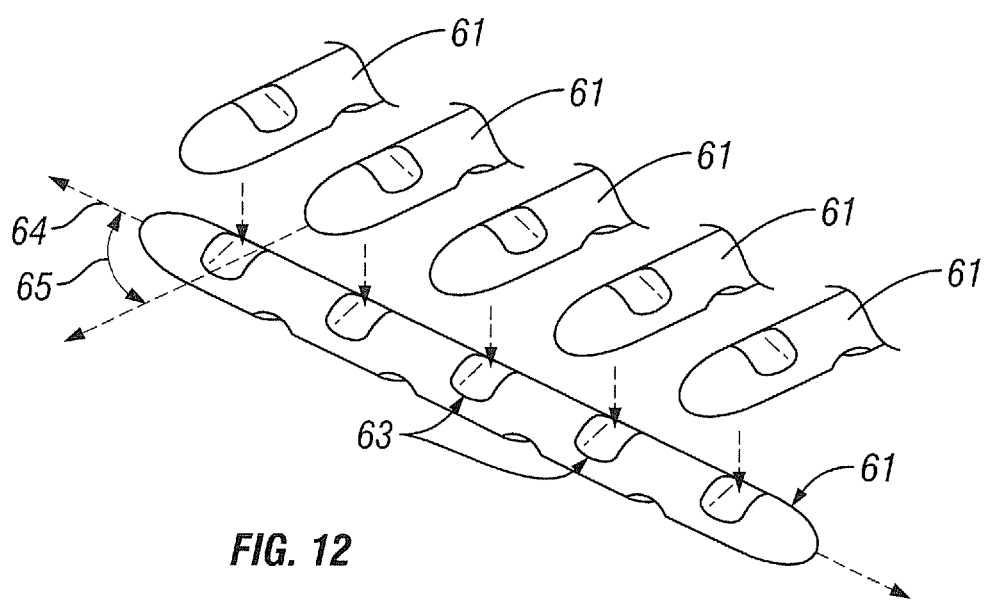
Figure 13:
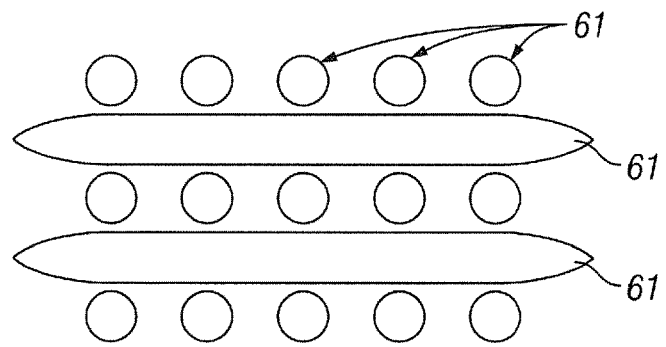

Referring to FIGS. 10-13, another method or system 60 according to the invention is shown. According to one embodiment of system 60, a plurality of modified pins 61 may be sequentially inserted into a fractured vertebral body, as shown in FIGS. 10-11. As best seen in FIG. 12, pins 61 are configured and dimensioned similar to pin 62 described above, except one or more grooves, troughs, or indentations 63 may extend transverse to longitudinal axis 64. In this regard, pins 61 function similar to pins 62 and also facilitate cross stacking and scaffold formation when pins 61 are inserted at different angles into the vertebral body (FIG. 13). For example, as shown in FIGS. 10-11, pins 61 may be inserted through a cannula 44 extending through both the left and right pedicles of a vertebral body. For example, a plurality of pins 61 may be inserted through the left pedicle into the vertebral body and are generally oriented in a first direction and one or more pins 61 may be inserted through the other pedicle to be generally oriented in a second direction angled with respect to the first direction. In one embodiment, pins 61 may be angled between about 45 and 135 degrees. As pins 61 inserted via, each pedicle are angled with respect to the pins inserted via the other pedicle, a grid or crossing pattern or scaffold structure may result as the pins 61 tend to orient or ride within the troughs or indentations 63 of the adjacent pins. At the same time, as the volume of the vertebral body is filled with pins 61, a vertical decompressive force is gradually transmitted to the end plates to force the end plates apart and decompress the compression fracture, as shown in FIG. 11. Those skilled in the art may appreciate the vast customizability of such a system, as a surgeon practitioner may selectively install any number of pins 61 at any number of locations within the vertebral body. In addition, gradual and or precise controlled expansion of the vertebral body may be achieved as each individual pin 61 is installed. Moreover, as pins 61 tend to locate within indentations 63 controlled stacking and/or minimization of post insertion motion may be achieved. According to another embodiment, pins 61 may be used in combination with any other type of pins 42, 62, described herein, whether partially threaded, completely threaded, or entirely nonthreaded, as desired. For example, a plurality of pins 61 may be inserted through one pedicle into the vertebral body and oriented in one general direction and one or more different types of pins 42, 62 may be inserted through the other pedicle to be oriented in a different direction. In still other embodiments, any combination of pins may be inserted via either or both pedicles.

According to one variation, indentations 63 may be positioned at varied transverse angles 65 with respect to axis 64. Angle 65 may be between about 45 and 135 degrees. In one embodiment, when multiple indentations 63 are provided along the length of pin 61, angles 65 may vary along the length of pin 61 such that indentations toward the center of pin 61 are positioned at a different angle 65 than indentations toward the ends. In this regard, when such indentation angles are used, a splayed pattern or matrix may be created which may have a more arcuate peripheral shape and be more conforming to the interior shape of a vertebral body.

The materials used in constructing system 40, pins 42, 62, and cannula 44 and the other devices described herein may comprise any of a wide variety of biocompatible materials. in certain embodiments, a radiopaque material, such as metal (e.g., stainless steel, titanium alloys, or cobalt alloys) or a polymer (e.g., ultra high molecular weight polyethylene) may be used, as is well know in the art, in alternate embodiments, a radiolucent material, such as polyetheretherketone (PEEK) may be used. When flowable or other filler material is desired, polymethylmethacrylate (PMMA) may be used In other alternate embodiments, a generally porous or microsphere material may be used as a filler material. Exemplary microsphere material that may be used is disclosed in U.S. patent application Ser. No. 11/552,244, filed Oct. 24, 2006 and entitled "Porous and Nonporous Materials for Tissue Grafting and Repair," the entire contents of which are incorporated herein by reference.

Figure 14:
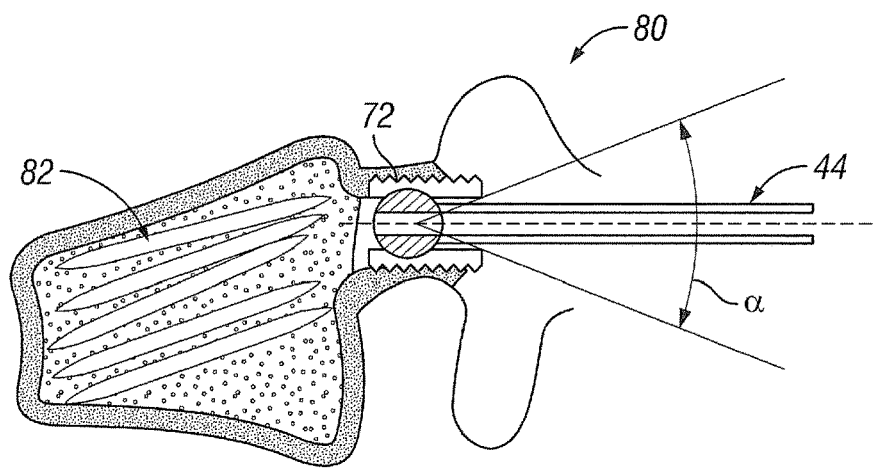
FIGS. 14-15 are side views of another embodiment of a bone treatment system according to the invention.
Figure 15:
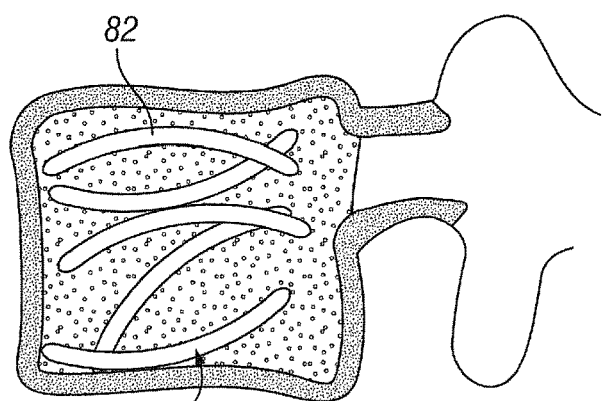

Referring to FIGS. 14-15, another embodiment of a system 80 according to the invention is shown. System 80 is similar to system 40 described above, except shape memory alloy, such as nitinol may be used. Pins 82 are generally made from memory alloy that resumes a predefined shape when exposed to heat or other triggering methods. In this regard, pins 82 may have a first shape that is generally straight and a second shape that is generally curved. in one variation, when pins 82 are generally straight, the may have a shape or profile similar to pins 62 shown in FIG. 7. As with previously described embodiments, pins 82 may be forcibly advanced into an interior of a vertebral body through a minimally invasive technique such as through a working cannula 44 and packed into the interior of a vertebral body while straight and within the vertebral body the pins may resume their curved shape, as shown in FIG. 15, triggering expansion in the vertical direction to create a vertical or expansive force to thereby reduce a vertebral compression fracture and restore height to the vertebral body. Such an arch shape of pins 82 will occur when pins 82 are exposed to body temperature, returning the shape memory material to its memorized shape.

Figure 16:
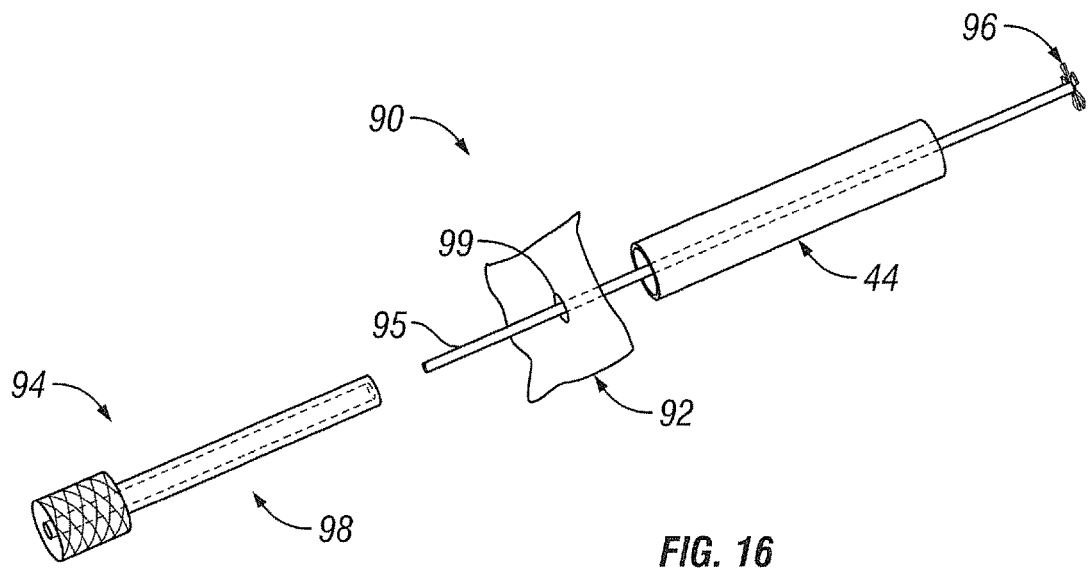
FIGS. 16-17 are side views of another embodiment of a bone treatment system according to the invention.
Figure 17:
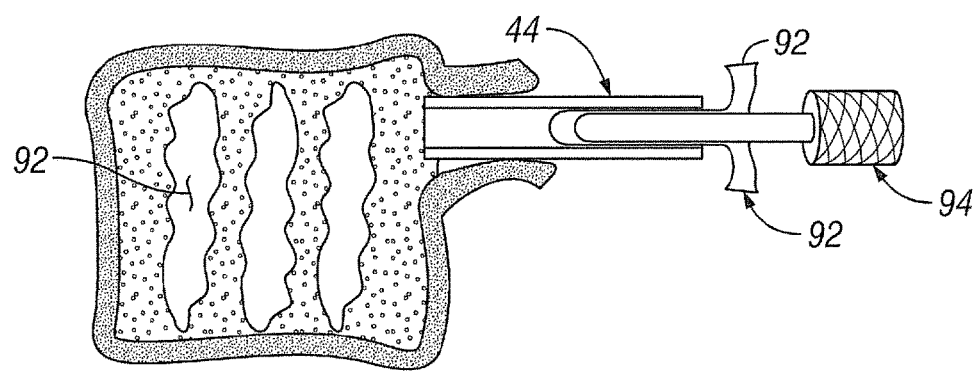

Referring to FIGS. 16-17, another embodiment of a bone fracture treatment system 90 is shown. System 90 generally comprises a plurality of flexible membranes or thin sheets 92 advanceable through cannula 44 into a vertebral body to be treated. In one embodiment, sheets 92 may be made from bone or other natural tissue. According to one embodiment, the sheet bone or tissue can have varied densities for forming a harder or softer filling. In another variation, sheets 92 may be made from a generally flexible yet resilient material, including, but not limited to, cloth, mesh any or other flexible elastic plastic or synthetic material, such as polyurethane. Any biocompatible material may also be used that has the ability to be inserted in a cannulated tube and inserted in the vertebral body. As best seen in FIG. 17, sheets 92 may be thin wafer like members that are flexible enough to be folded or curved to fit down a cannula, yet resilient enough to reform or spring back to a more straightened shape once inserted into the vertebral body. Sheets 92 may be packed or inserted into the interior of a vertebral body to facilitate and/or transfer lateral force or to expand in a vertical direction and create a vertical or expansive force to thereby reduce a vertebral compression fracture. As with previous embodiments, system 90 may be used in a minimally invasive procedure and in one embodiment sheets 92 may be fed down a tube or portal 44, as shown in FIG. 16. In one variation sheets 92 may be fed using a plunger 94. In one variation, plunger 94 may have a wire 95 with an umbrella like stopper 96 at a distal end thereof extending through a central hole 99 of sheets 92. Plunger 94 may have a pusher portion 98 adjacent a proximal end to facilitate pushing or inserting sheets 92 through cannula 44 into the vertebral body. According to one variation, stopper 96 may be made from a biocompatible implantable material and stopper 96 may be detached or cut from plunger 94 to remain implanted in the body.

Figure 18:
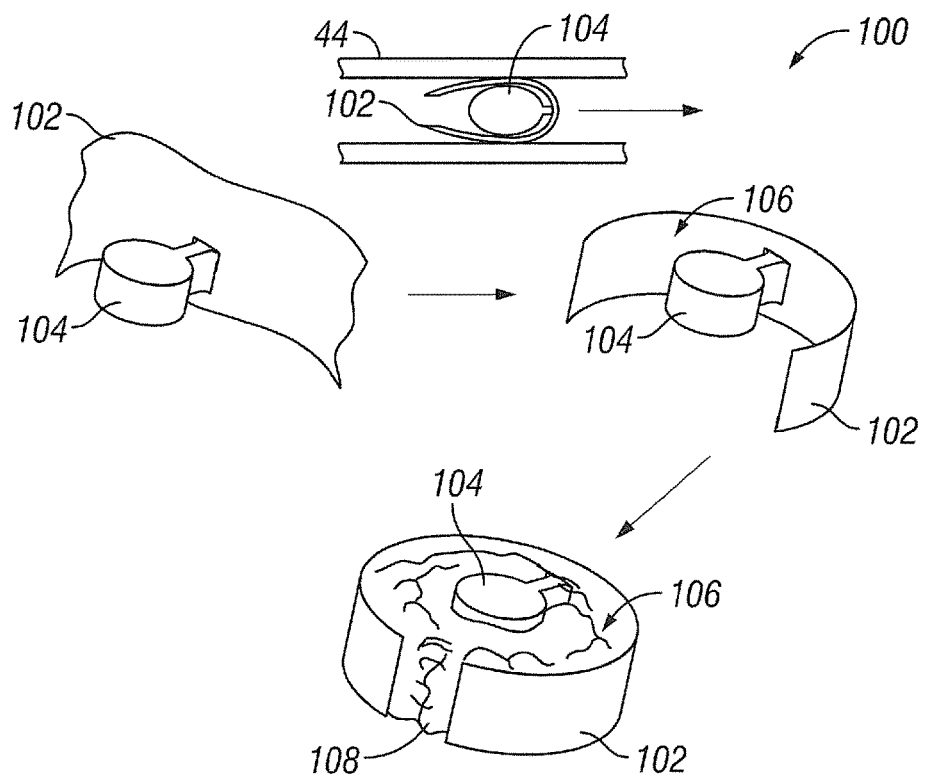
FIGS. 18-19 are views of another embodiment of a bone treatment system according to the invention.
Figure 19:
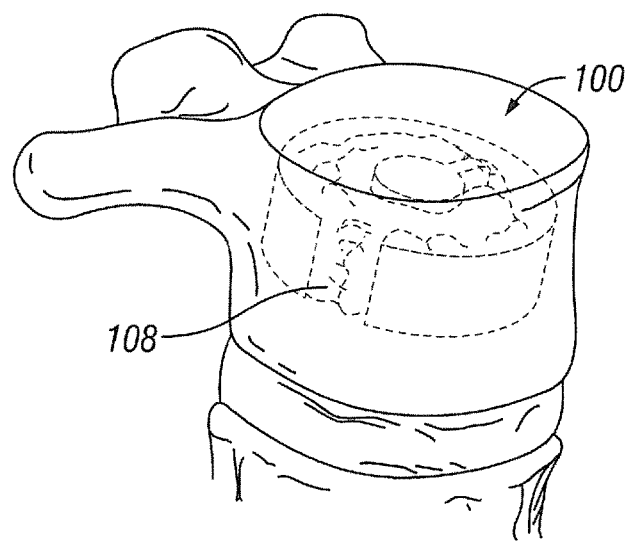

Referring to FIGS. 18-19, another embodiment of a bone treatment system or device 100 is shown. System 100 is similar to system 90 described above, except the membrane 102 may be integral with, connected to, or otherwise disposed about a central hub 104. As with previous embodiments, system 100 may be used in a minimally invasive procedure and in one embodiment sheets 102 may be fed down a tube or portal 44, as shown in FIG. 18. In this regard, as with prior embodiments, membrane 102 and hub 104 may be made from bone or other natural tissue or any other generally flexible yet resilient material, including, but not limited to, cloth, mesh any or other flexible elastic plastic or synthetic material, such as polyurethane. Any biocompatible material may also be used that has the ability to be inserted in a cannulated tube and inserted in the vertebral body. Central hub portion 104 has a general cylindrical shape and may facilitate radial expansion of membrane 102 once installed in a vertebral body. Membrane 102 may have a ring or cylindrical peripheral shape and/or be otherwise configured and dimensioned to radially enclose an area or central region 106 within bone. In this regard, the enclosed area may be filled with any known flowable material 108, including but not limited to bone cement. In one variation, membrane 102 forms a. radial barrier preventing any flowable material to flow radially through membrane 102. In another variation, when used to treat a vertebral compression fracture, membrane 102 may be radially expanded to abut or contact the inner walls of the cortical bone of a vertebral body. Openings may be provided adjacent the top and bottom to allow flowable material to contact the interior of the upper and lower endplate of the vertebral body being treated. According to one variation, a porous filler material, such as a microsphere material may be used. Exemplary microsphere material that may be used with system 100 is disclosed in U.S. patent application Ser. No. 11/552,244, filed Oct. 24, 2006 and entitled "Porous and Nonporous Materials for Tissue Grafting and Repair," the entire contents of which are incorporated herein by reference. The device may be deployed or expanded within the vertebra by inserting or injecting a flowable material and/or a plurality of microsphere members to trigger expansion of device 1100 to create a radially constrained vertical or expansive force to thereby reduce a vertebral compression fracture. In certain embodiments, wall membrane 102 may be defined with a limited flexibility such that it may expand to enclose a maximum volume of the central region 106 and prevent overexpansion. In this regard, wall membrane 102 may be designed and configured to expand to conform to the interior volume of an intact healthy vertebral body of a particular patient as desired or diagnosed by a practitioner user.

Figure 20:
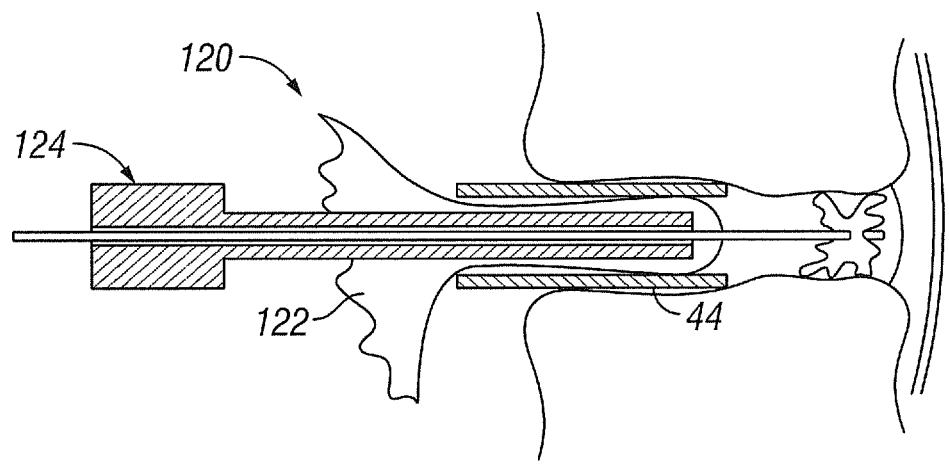
FIGS. 20-21 are views of one embodiment of a minimally invasive disc treatment system according to the invention.
Figure 21:
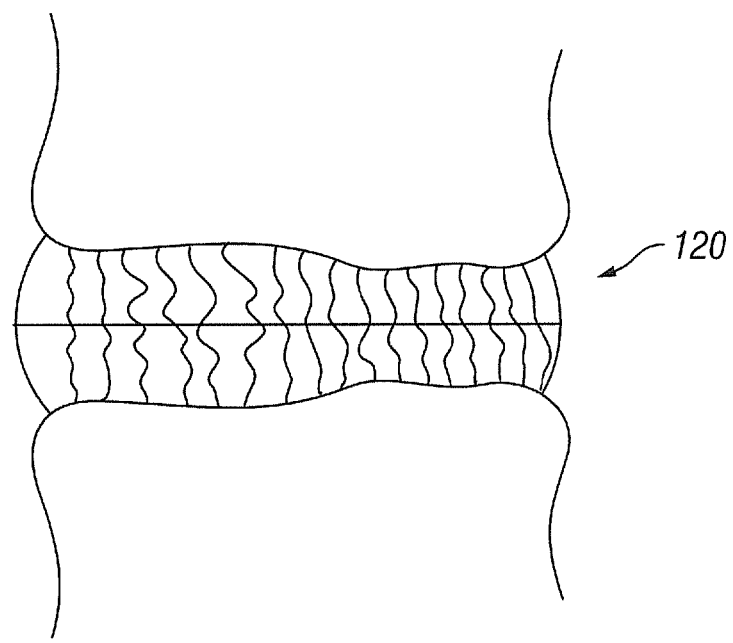

Referring now to FIGS. 20-21, an alternative embodiment of a minimally invasive spine treatment system 120 is shown. System 120 is similar to system 90 described above, except it is adapted to be inserted or implanted in the disc space between adjacent vertebral bodies. System 120 generally comprises a plurality of flexible membranes or thin sheets 122 advanceable through cannula 44 into a disc space to be treated. Sheets 122 may be made from bone or other natural tissue or any other generally flexible yet resilient material, including, but not limited to, cloth, mesh any or other flexible elastic plastic or synthetic material, such as polyurethane. Any biocompatible material may also be used that has the ability to be inserted in a cannulated tube and inserted in the disc space. Sheets 122 may be thin wafer like members that are flexible enough to be folded or curved to fit down a cannula, yet resilient enough to reform or spring back to a more straightened shape once inserted into the disc space. In one variation, sheets 122 may be packed or inserted into the disc space to facilitate and/or transfer lateral force or to expand in a vertical direction and create a vertical or expansive force to thereby space apart adjacent vertebrae and/or decompress an adjacent nerve. As with previous embodiments, system 120 may be used in a minimally invasive procedure and in one embodiment sheets 122 may be fed down a tube or portal 44, as shown in FIG. 20. In one variation sheets 122 may be fed using a plunger 124 similar to plunger 94, described above, to facilitate pushing or inserting sheets 122 through cannula 44 into the disc space.

Figure 22:
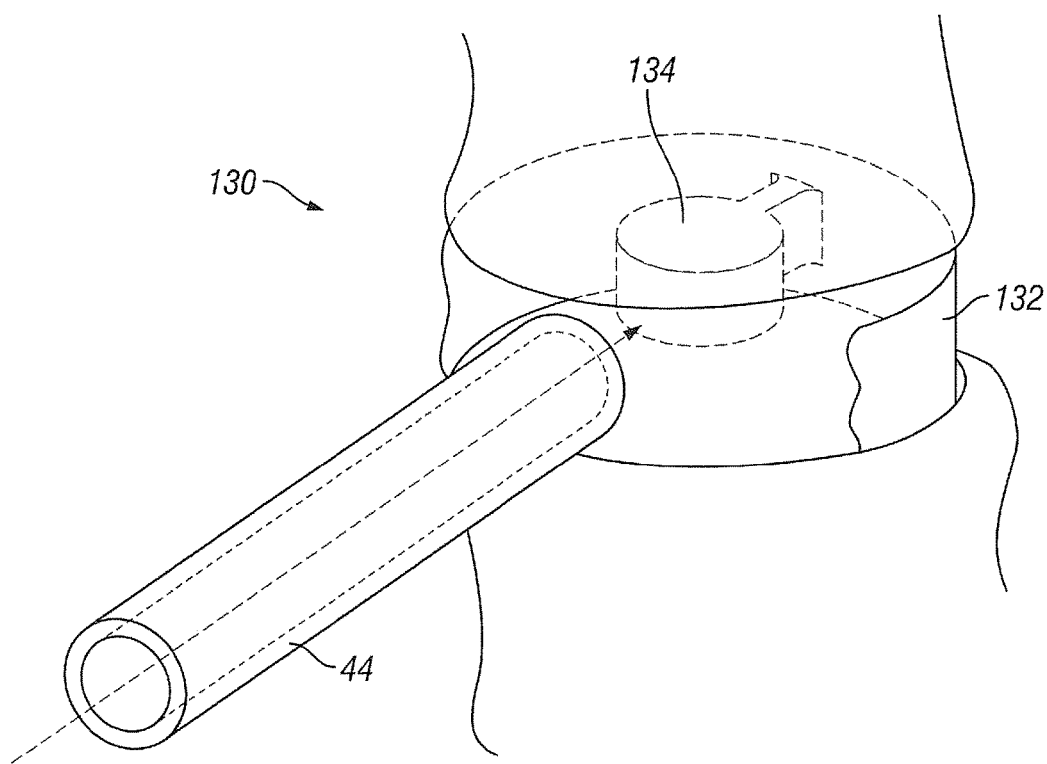
FIG. 22 is a side view of another embodiment of a minimally invasive disc treatment system according to the invention.

Referring now to FIG. 22, an alternative embodiment of a minimally invasive spine treatment system 130 is shown. System 130 is similar to system 100 described above, except it is adapted to be inserted or implanted in the disc space between adjacent vertebral bodies. Membrane 132 may be integral with, connected to, or otherwise disposed about a central hub 134. Membrane 132 and hub 134 may be fed down a tube or portal 44 and, as with prior embodiments, membrane 132 and hub 134 may be made from bone or other natural tissue or any other generally flexible yet resilient material, including, but not limited to, cloth, mesh any or other flexible elastic plastic or synthetic material, such as polyurethane. Any biocompatible material may also be used that has the ability to be inserted in a cannulated tube and inserted in the disc space. Central hub portion 134 has a general cylindrical shape and may facilitate radial expansion of membrane 132 once installed in a disc space. Membrane 132 may have a ring or cylindrical peripheral shape and/or be otherwise configured and dimensioned to radially enclose an area or central region 136 within bone. In this regard, the enclosed area may be filled with any known flowable material 138, including but not limited to bone cement. In one variation, membrane 132 forms a radial barrier preventing any flowable material to now radially through membrane 102. Openings may be provided adjacent the top and bottom to allow flowable material to contact the upper and/or lower endplates of the adjacent vertebral bodies of the disc space being treated. According to one variation, a porous filler material, such as a microsphere material may be used. Exemplary microsphere material that may be used with system 100 is disclosed in U.S. patent application Ser. No. 11/552,244, filed Oct. 24, 2006 and entitled "Porous and Nonporous Materials for Tissue Grafting and Repair," the entire contents of which are incorporated herein by reference. The device may be deployed or expanded within the disc space by inserting or injecting a flowable material and/or a plurality of microsphere members to trigger expansion of device 130 to create a radially constrained vertical or expansive force to thereby space apart adjacent vertebrae and/or decompress an adjacent nerve. In certain embodiments, wall membrane 132 may be defined with a limited flexibility such that it may expand to enclose a maximum volume of the central region 136 and prevent overexpansion. In this regard, wall membrane 132 may be designed and configured to expand to conform to the interior volume of an intact healthy vertebral disc of a particular patient as desired or diagnosed by a practitioner user.

While it is apparent that the invention disclosed herein is well calculated to fulfill the objects stated above, it will be appreciated that numerous modifications and embodiments may be devised by those skilled in the art.

What is claimed is:

1. A method of spine surgery comprising:
   forming an incision in a vertebral body, the vertebral body having an upper endplate and a lower endplate;
   positioning a cannula adjacent to the vertebral body;
   inserting a first pin extending from a proximal end to a distal end into the vertebral body through the cannula, wherein the entire first pin extending from the proximal end to the distal end resides in the vertebral body;
   inserting a second pin into the vertebral body through the cannula, wherein the second pin is placed into the vertebral body at an angle different from the first pin, wherein the first pin and the second pin assist in the displacement of at least one of the upper or lower endplate of the vertebral body,
   wherein the cannula includes one or more openings disposed along a length of the cannula, the one or more openings configured to facilitate angled entry of at least one of the first pin and the second pin; and
   removing the cannula such that the first and second pins remain within the vertebral body.

2. The method of claim 1, wherein the first pin and the second pin assist in the displacement of an upper or lower endplate of the vertebral body.

3. The method of claim 1, wherein the cannula comprises a threaded end piece.

4. The method of claim 3, wherein the threaded end piece of the cannula allows the cannula to be docked in the pedicle.

5. The method of claim 1, wherein the first pin is threaded.

6. The method of claim 5, wherein the first pin is only partly threaded along a shaft of the first pin.

7. The method of claim 5, wherein the first pin is completely threaded along a shaft of the first pin.

8. The method of claim 1, further comprising inserting a third pin into the cannula to assist in the displacement of an upper or lower endplate of the vertebral body.

9. A method of spine surgery comprising:
   forming an incision in a vertebral body, the vertebral body having an upper endplate and a lower endplate;
   positioning a cannula adjacent to the incision of the vertebral body;
   inserting a first pin extending from a proximal end to a distal end into the vertebral body through the cannula, wherein the entire first pin extending from the proximal end to the distal end resides in the vertebral body;
   adjusting the position of the cannula relative to the incision;
   inserting a second pin into the vertebral body through the cannula, wherein the second pin is inserted at a different trajectory from the first pin,
   wherein the first pin and the second pin assist in the displacement of at least one of the upper or lower endplate of the vertebral body,
   wherein the cannula includes one or more openings disposed along a length of the cannula, the one or more openings configured to facilitate angled entry of at least one of the first pin and the second pin; and
   removing the cannula such that the first and second pins remain within the vertebral body.

10. The method of claim 9, wherein the cannula comprises a threaded exterior portion.

11. The method of claim 10, further comprising threadedly advancing the threaded exterior portion of the cannula into the incision to dock the cannula within the incision.

12. The method of claim 9, wherein the cannula comprises a proximal portion and a distal portion, wherein the distal portion is movably connected to the proximal portion such that the cannula may angulate or rotate with respect to the distal portion.

13. The method of claim 9, wherein adjusting the position of the cannula comprises moving it between 30 to 60 degrees from a prior position.

14. The method of claim 9, wherein the first pin and the second pin are used to push the vertebral body in an outward direction to displace an upper or lower end plate of the vertebral body.

15. The method of claim 9, wherein the first pin comprises threads.

16. The method of claim 15, wherein the first pin is completely threaded along a shaft.

17. The method of claim 9, further comprising inserting a third pin and a fourth pin into the vertebral body.

18. The method of claim 9, wherein the incision is formed through a pedicle.

19. The method of claim 1, wherein the first or second pin is made of a shape memory alloy and the first or second pin has a first shape that is generally straight and a second shape that is generally curved.

\* \* \* \* \*